United States Patent [19]

Heerze et al.

[11] Patent Number: 5,635,606
[45] Date of Patent: Jun. 3, 1997

[54] METHOD OF BINDING AND REMOVING TOXIN A

[75] Inventors: Louis D. Heerze; Glen D. Armstrong, both of Edmonton, Canada

[73] Assignee: Synsorb, Biotech Inc., Alberta, Canada

[21] Appl. No.: 450,572

[22] Filed: May 25, 1995

Related U.S. Application Data

[63] Continuation of Ser. No. 195,009, Feb. 14, 1994, Pat. No. 5,484,773.
[51] Int. Cl.$^6$ .......................... A23J 1/00; G01N 33/569; C12Q 1/04
[52] U.S. Cl. .......................... 530/412; 435/4; 435/38; 530/350
[58] Field of Search .......................... 435/7.32, 9, 38; 514/23; 530/350, 412

[56] References Cited

U.S. PATENT DOCUMENTS

| | | | |
|---|---|---|---|
| 4,137,401 | 1/1979 | Lemieux et al. | 536/116 |
| 4,238,473 | 12/1980 | Lemieux et al. | 536/1.11 |
| 4,362,720 | 12/1982 | Lemieux et al. | 514/25 |
| 4,713,240 | 12/1987 | Wilkins et al. | 424/239.1 |
| 4,863,852 | 9/1989 | Wilkins et al. | 435/7.25 |
| 5,079,353 | 1/1992 | Ratcliffe et al. | 536/53 |
| 5,098,826 | 3/1992 | Wilkins et al. | 435/7.32 |
| 5,266,315 | 11/1993 | Taguchi et al. | 424/93.41 |

FOREIGN PATENT DOCUMENTS

| | | |
|---|---|---|
| 319253 | 6/1989 | European Pat. Off. |
| 2857790 | 12/1983 | Germany |
| WO93/08209 | 4/1993 | WIPO |

OTHER PUBLICATIONS

International Search Report mailed on Jun. 30, 1995 in connection with counterpart PCT International Application No. PCT/CA95/00060.

Abbas, S.A., et al., "Tumor–Associated Oligosaccharides I: Synthesis of Sialyl–Lewis$^a$ Antigenic Determinant", Sialic Acids, Proc. Japan–German Symp. Berlin 22–23 (1988).

Amvam–Zollo, P., et al., "Streptococcus pneumoniae Type XIV Polysaccharide: Synthesis of a Repeating Branched Tetrasaccharide with Dioxa–Type Spacer–Arms", Carbohydrate Research, 150:199–212 (1986).

Armstrong, GD, et al., "Investigation of shiga–like toxin binding to chemically synthesized oligosaccharide sequences", J. Infect. Dis., 164:1160–7 (1991).

Barbut, F, et al., "Comparison of enterotoxin production, cytotoxin production, serogrouping and antimicrobial susceptibilities of Clostridium difficile strains isolated from AIDS and human immunodeficiency virus–negative patients", J. Clin. Microbiol. 31:740–2 (1993).

Bartlett, JG, et al., "Symptomatic relapse after oral vancomycin therapy of antibiotic–associated pseudomembranous colitis", Gastroenterology, 78:431–4 (1980).

Bartlett, JD, "Treatment of antibiotic–associated pseudomembranous colitis", Rev. Infect. Dis., 6, Suppl. 1:S235–41 (1984).

Bartlett, JG, et al., "Antibiotic–associated pseudomembranous colitis due to toxin–producing clostridia",N. Engl. J. Med. 298:531–534 (1978).

Chernyak, A. Y., et al., "A New Type of Carbohydrate–Containing Synthetic Antigen: Synthesis of Carbohydrate–Containing Polyacrylamide Copolymers having the Specificity of 0:3 and 0:4 Factors of Salmonella", Carbohydrate Research, 128: 269–282 (1984).

Clark, GF, et al., "Toxin A from Clostridium difficile binds to rabbit erythrocyte glycolipids with terminal αGal(1–3)βGal(14)βGlcNAc sequences", Arch. Biochem. Biophys., 257:217–29 (1987).

Cox, D., et al. "A New Synthesis of 4–O–α–D–Galactopyranosyl–D–Galacto–Pyranose", Carbohy. Res., 62: 245–252 (1978).

Cozart, JC, et al., "Clostridium difficile diarrhea in patients with AIDS versus non–AIDS controls. Method of treatment and clinical response to treatment", J. Clin. Gastroenterol. 16:192–4 (1993).

Dahmén, J., et al., "2–Bromoethyl glycosides: applications in the synthesis of spacer–arm glycosides," Carbohydrate Research, 118: 292–301 (1983).

Dahmén, J., et al., "Synthesis of space arm, lipid, and ethyl glycosides of the trisaccharide portion [α–D–Gal(1–4)–β–D–Gal–(1–4)–β–D–Glc] of the blood group p$^k$ antigen: preparation of neoglycoproteins", Carbohydrate Research, 127: 15–25 (1984).

Ekborg, G., et al., "Synthesis of Three Disaccharides for the Preparation of Immunogens bearing Immunodeterminants Known to Occur on Glycoproteins", Carbohydrate Research, 110: 55–67 (1982).

Eveillard, M. et al., "Identification and characterization of adhesive factors of Clostridium difficile involved in adhesion to human colonic enterocyte–like Caco–2 and mucus–secreting HT29 cells in culture", Molecular Microbiology, 7: 371–381 (1993).

Fernandez–Santana, V., et al., "Glycosides of Monoallyl Diethylene Glycol. A New type of Spacer group for Synthetic Oligosaccharides", J. Carbohydrate Chemistry, 8(3), 531–537 (1989).

Finegold, SM, et al., "Therapy directed against Clostridium difficile and its toxins. Complications of therapy". In Rolfe, R.D. et al. (eds) C.difficile: It's Role in Intestinal Disease, Academic Press, Inc., San Diego, CA 341–57 (1988).

(List continued on next page.)

Primary Examiner—Elli Peselev
Attorney, Agent, or Firm—Burns, Doane, Swecker & Mathis, L.L.P.

[57] ABSTRACT

This invention relates to treatment of antibiotic associated diarrhea, including Clostridium difficile associated diarrhea (CDAD) and pseudomembranous colitis (PMC), using oligosaccharide compositions which bind C. difficile toxin A. More specifically, the invention concerns neutralization of C. difficile toxin A associated with CDAD.

3 Claims, 4 Drawing Sheets

OTHER PUBLICATIONS

Fügedi, P., et al., "Thioglycosides as Glycosylating Agents in Oligosaccharide Synthesis", Glycoconjugate J., 4:97–108 (1987).

Garegg, P. J., et al., "A Synthesis of 8-Methoxycarbonyloct-1-yl O-α-Galactopyranosyl-(1→3)-O-β-D-Galactopyranosyl-(1→4)-2-Acetamido-2-Deoxy-β-D-Glucopyranoside", Carbohy. Res., 136: 207–213 (1985).

Garegg, P. J., et al., "Synthesis of 6-and 6'-deoxy derivatives of methyl 4-0-α-D-galactopyranosyl-β-D-galactopyranoside for studies of inhibition of pyelonephritogenic fimbriated E. coli adhesion to urinary epithelium–cell surfaces", Carbohy. Res., 137: 270–275 (1985).

Heerze, et al., "Oligosaccharide sequences attached to an inert support (SYNSORB) as a potential therapy for antibiotic associated diarrhea and pseudomonous colitis," J.Infect.Dis. 169: 1291–1296, Jun. 1994.

Heerze, et al., "Utilization of oligosaccharide sequences attached to an inert support (SYNSORB) as a potential therapy for antibiotic associated diarrhea and pseudomonous colitis," Abs.Gen.Soc.Micro. 46: Abs 120965, 25 May 1994.

Jacquinet, J. C., et al., "Synthesis of Blood–group Substances, Part 11. Synthesis of the Trisaccharide O-α-D-Galactopyranosyl-(1→3)-0-β-D-galactopyranosyl-(1→4)-2-acetamido-2-deoxy-D-glucopyranose", J.C.S. Perkin, I: 326–330 (1981).

Kameyama, A., et al., "Total synthesis of sialyl Lewis X", Carbohydrate Res., 209: c1–c4 (1991).

Kamiya, S, et al., "Analysis of purity of Clostridium difficile toxin A derived by affinity chromatography on immobilized bovine thyroglobulin", FEMS Microbiol. Lett., 56:331–6 (1988).

Keighley, MRB, "Antibiotic–associated pseudomembranous colitis: pathogenesis and management", Drugs, 20:449–56 (1980).

Koike, K., et al., "Total Synthesis of Globotriaosyl-E and Z-Ceramides and Isoglobotriaosyl-E-Ceramide," Carbohydr. Res., 163: 189–208 (1987).

Kushnaryov, V.M., et al., "Effect of Clostridium difficile Enterotoxin A on Ultrastructure of Chinese Hamster Ovary Cells", Infection and Immunity, 57: 3914–3921 (1989).

Krivan, HC, et al., "Cell surface binding site for Clostridium difficile enterotoxin: evidence for a glycoconjugate containing the sequence αGal(1-3)βGal(1-4)βGlcNAc", Infect. Immun., 53:573–81 (1986).

Krivan, HC, et al., "Purification of Clostridium difficile toxin A by affinity chromatography on immobilized bovine thyroglobulin", Infect. Immun., 55:1873–7 (1987).

Lee, R.T., et al., "Synthesis of 3-(2-Aminoethylthio) PropylGlycosides", Carbohydrate Research, 37: 193–201 (1974).

Lemieux, RU, et al., "The properties of a 'synthetic' antigen related to the blood–group Lewis A", J. Am. Chem. Soc., 97:4076–83 (1975).

Lyerly, DM, et al., "Clostridium difficile: Its Disease and Toxins", Clinical Microbiology Reviews, 1 :18 (1988).

Lyerly, DM. "Epidemiology of Clostridium difficile disease", Clin. Microbiol. News 15:49–53 (1993).

Okamoto, K., et al., "Glycosidation of Sialic Acid," Tetrahedron, 47: 5835–5857 (1990).

Onderdonk, AB, et al., "Comparative effects of clindamycin and clindamycin metabolites in the hamster model for antibiotic–associated colitis", J. Antimicrob. Chem., 8:383–93 (1981).

Paulsen, "Advances in Selective Chemical Syntheses of Complex Oligosaccharides", Angew. Chem. Int. Ed. Eng., 21:155–173 (1982).

Paulsen, H., "Synthese von oligosaccharid–determinante-mit amid–spacer vom typ des T–antigens", Carbohydr. Res., 104:195–219 (1982).

Rana, S. S., et al., "Synthesis of Phenyl 2-Acetamido-2-Deoxy-3-O-α L-Fucopyranosyl-β-D-Glucopyranoside and Related Compounds", Carbohydrate Research, 91: 149–157 (1981).

Schaubach, R., et al., "Tumor–Associated Antigen Synthesis: Synthesis of the Gal-α-(1→3)-Gal-β-(1→4)-GlCNAc Epitope. A specific Determinant for Metastatic Progression?," Liebigs Ann. Chem., 607–614 (1991).

Schmidt, "New Methods for the Synthesis of Glycosides and Oligosaccharides—Are There Alternatives to the Koenigs–Knorr Method?" Angew. Chem. Int. Ed. Eng., 25:212–235 (1986).

Sullivan, NM, et al.,"Purification and characterization of toxin A and B from Clostridium difficile", Infect. Immun., 35:1032–40 (1983).

Tedesco, FJ, "Pseudomembranous colitis: Pathogenesis and therapy", Med. Clin. North Am., 66:655–64 (1982).

Triadfilopoulos, G, et al., "Differential effects of Clostridium difficile toxin a and b on rabbit ileum", Gastroenterology, 93:273–9 (1987).

Tucker, KD, et al., "Toxin A of Clostridium difficile binds to carbohydrate antigens I, X, and Y", Infect. Immun., 59:73–8 (1991).

Von Eichel–Streiber, C., et al., "Clostridium difficile toxin A carries a c–terminal repetititve structure homologous to the carbohydrate binding region of streptococcal glycosyltransferases", Gene, 96:107–13 (1990).

SYNSORB Neutralization of Toxin A Activity

FIG. 1

METHOD OF BINDING AND REMOVING TOXIN A

This application is a continuation of application Ser. No. 08/195,009, filed Feb. 14, 1994, now U.S. Pat. No. 5,484,773.

FIELD OF THE INVENTION

This invention relates to treatment of antibiotic associated diarrhea, including *Clostridium difficile* associated diarrhea (CDAD) and pseudomembranous colitis (PMC). More specifically, the invention concerns neutralization of *C. difficile* toxin A associated with CDAD.

REFERENCES

The following references are cited in the application as numbers in brackets ([ ]) at the relevant portion of the application.

1. Bartlett, J. G., et al., "Antibiotic-associated pseudomembranous colitis due to toxin-producing clostridia", N. Engl. J. Med. 298:531–534 (1978).
2. Lyerly, D. M., "Epidemiology of *Clostridium difficile* disease", Clin. Microbiol. News 15:49–53 (1993).
3. Cozart, J. C., et al., "*Clostridium difficile* diarrhea in patients with AIDS versus non-AIDS controls. Method of treatment and clinical response to treatment", J. Clin. Gastroenterol. 16:192–4 (1993).
4. Barbut, F., et al., "Comparison of enterotoxin production, cytotoxin production, serogrouping and antimicrobial susceptibilities of *Clostridium difficile* strains isolated from AIDS and human immunodeficiency virus-negative patients", J. Clin. Microbiol. 31:740–2 (1993).
5. Krivan, H. C., et al., "Cell surface binding site for *Clostridium difficile* enterotoxin: evidence for a glycoconjugate containing the sequence αGal(1-3)βGal(1-4) βGlcNAc", Infect. Immun., 53:573–81 (1986).
6. Clark, G. F., et al., "Toxin A from *Clostridium difficile* binds to rabbit erythrocyte glycolipids with terminal αGal (1-3)βGal(1-4)βGlcNAc sequences", Arch. Biochem. Biophys., 257:217–29 (1987).
7. Tucker, K. D., et al., "Toxin A of *Clostridium difficile* binds to carbohydrate antigens I, X, and Y", Infect. Immun., 59:73–8 (1991).
8. Krivan, H. C., et al., "Purification of *Clostridium difficile* toxin A by affinity chromatography on immobilized bovine thyroglobulin", Infect. Immun., 55:1873–7 (1987).
9. Kamiya, S., et al., "Analysis of purity of *Clostridium difficile* toxin A derived by affinity chromatography on immobilized bovine thyroglobulin", FEMS Microbiol. Lett., 56:331–6 (1988).
10. Armstrong, G. D., et al., "Investigation of shiga-like toxin binding to chemically synthesized oligosaccharide sequences", J. Infect. Dis., 164:1160–7 (1991).
11. Von Eichel-Streiber, C., et al., "*Clostridium difficile* toxin A carries a c-terminal repetitive structure homologous to the carbohydrate binding region of streptococcal glycosyltransferases", Gene, 96:107–13 (1990).
12. Lemieux, R. U., et al., "The properties of a 'synthetic' antigen related to the blood-group Lewis A", J. Am. Chem. Soc., 97:4076–83 (1975).
13. Sullivan, N. M., et al., "Purification and characterization of toxin A and B from *Clostridium difficile*", Infect. Immun., 35:1032–40 (1983).
14. Finegold, S. M., et al., "Therapy directed against *Clostridium difficile* and its toxins. Complications of therapy". In Rolfe, R. D. et al. (eds) *C. difficile*: It's Role in Intestinal Disease, Academic Press, Inc., San Diego, Calif. 341–57 (1988).
15. Bartlett, J. G., et al., "Symptomatic relapse after oral vancomycin therapy of antibiotic-associated pseudomembranous colitis", Gastroenterology, 78:431–4 (1989).
16. Tedesco, F. J., "Pseudomembranous colitis: Pathogenesis and therapy", Med. Clin. North Am., 66:655–64 (1982).
17. Keighley, M. R. B., "Antibiotic-associated pseudomembranous colitis: pathogenesis and management", Drugs, 20:449–56 (1980).
18. Bartlett, J. D., "Treatment of antibiotic-associated pseudomembranous colitis", Rev. Infect. Dis., 6, Suppl. 1:1–55 (1984).
19. Onderdonk, A. B., et al., "Comparative effects of clindamycin and clindamycin metabolites in the hamster model for antibiotic-associated colitis", J. Antimicrob. Chem., 8:383–93 (1981).
20. Triadfilopoulos, G., et al., "Differential effects of *Clostridium difficile* toxin a and b on rabbit ileum", Gastroenterology, 93:273–9 (1987).
21. Lemieux, R. U., et al., "Glycoside-Ether-Ester Compounds", U.S. Pat. No. 4,137,401, issued Jan. 30, 1979.
22. Lemieux, R. U., et al., "Artificial Oligosaccharide Antigenic Determinants", U.S. Pat. No. 4,238,473, issued Dec. 9, 1980.
23. Lemieux, R. U., et al., "Synthesis of 2-Amino-2-Deoxyglycoses and 2-Amino-2-Deoxyglycosides from glycals", U.S. Pat. No. 4,362,720, issued Dec. 7, 1982.
24. Cox, D., et al. "A New Synthesis of 4-O-α-D-Galactopyranosyl-D-Galacto-Pyranose", Carbohy. Res., 62:245–252 (1978).
25. Dahmén, J., et al., "Synthesis of space arm, lipid, and ethyl glycosides of the trisaccharide portion [α-D-Gal-(1-4)-β-D-Gal(1-4)-β-D-Glc] of the blood group $p^k$ antigen: preparation of neoglycoproteins", Carbohydrate Research, 127:15–25 (1984).
26. Garegg, P. J., et al., "A Synthesis of 8-Methoxycarbonyloct-1-yl O-α-D-Galactopyranosyl-(1→3)-O-β-D-Galactopyranosyl-(1→4)-2-Acetamido-2-Deoxy-β-D-Glucopyranoside", Carbohy. Res., 136:207–213 (1985).
27. Garegg, P. J., et al., "Synthesis of 6- and 6'-deoxy derivatives of methyl 4-O-α-D-galactopyranosyl-β-D-galactopyranoside for studies of inhibition of pyelonephritogenic fimbriated *E. coli* adhesion to urinary epithelium-cell surfaces", Carbohy. Res., 137:270–275 (1985).
28. Jacquinet, J. C., et al., "Synthesis of Blood-group Substances, Part 11. Synthesis of the Trisaccharide O-α-D-Galactopyranosyl-(1→3)-O-β-D-galactopyranosyl-(1→4)-2-acetamido-2-deoxy-D-glucopyranose", J. C. S. Perkin, I.: 326–330 (1981).
29. Koike, K., et al., "Total Synthesis of Globotriaosyl-E and Z-Ceramides and Isoglobotriaosyl-E-Ceramide," Carbohydr. Res., 163: 189–208 (1987).
30. Schaubach, R., et al., "Tumor-Associated Antigen Synthesis: Synthesis of the Gal-α-(1→3)-Gal-β-(1→4)-GlCNAc Epitope. A specific Determinant for Metastatic Progression?," Liebigs Ann. Chem., 607–614 (1991).
31. Ratcliffe, R. M., et al., "Sialic Acid Glycosides, Antigens, Immunoadsorbents, and Methods for Their Preparation", U.S. Pat. No. 5,079,353, issued Jan. 7, 1992.
32. Okamoto, K., et al., "Glycosidation of Sialic Acid," Tetrahedron, 47:5835–5857 (1990).

33. Abbas, S. A., et al., "Tumor-Associated Oligosaccharides I: Synthesis of Sialyl-Lewis Antigenic Determinant", Sialic Acids, Proc. Japan-German Symp. Berlin 22–23 (1988).
34. Paulsen, "Advances in Selective Chemical Syntheses of Complex Oligosaccharides", Angew. Chem. Int. Ed. Eng., 21:155–173 (1982).
35. Schmidt, "New Methods for the Synthesis of Glycosides and Oligosaccharides—Are There Alternatives to the Koenigs-Knorr Method?" Angew. Chem. Int. Ed. Eng., 25:212–235 (1986).
36. Fügedi, P., et al., "Thioglycosides as Glycosylating Agents in Oligosaccharide Synthesis", Glycoconjugate J., 4:97–108 (1987).
37. Kameyama, A., et al., "Total synthesis of sialyl Lewis X", Carbohydrate Res., 209:c1–c4 (1991).
38. Ekborg, G., et al., "Synthesis of Three Disaccharides for the Preparation of Immunogens bearing Immunodeterminants Known to Occur on Glycoproteins", Carbohydrate Research, 110:55–67 (1982).
39. Dahmén, J., et al., "2-Bromoethyl glycosides: applications in the synthesis of spacer-arm glycosides," Carbohydrate Research, 118:292–301 (1983).
40. Rana, S. S., et al., "Synthesis of Phenyl 2-Acetamido-2-Deoxy-3-O-α L-Fucopyranosyl-β-D-Glucopyranoside and Related Compounds", Carbohydrate Research, 91:149–157 (1981).
41. Amvam-Zollo, P., et al., "Streptococcus pneumoniae Type XIV Polysaccharide: Synthesis of a Repeating Branched Tetrasaccharide with Dioxa-Type Spacer-Arms", Carbohydrate Research, 150:199–212 (1986).
42. Paulsen, H., "Synthese yon oligosaccharid-determinanten mit amid-spacer vom typ des T-antigens", Carbohydr. Res., 104:195–219 (1982).
43. Chernyak, A. Y., et al., "A New Type of Carbohydrate-Containing Synthetic Antigen: Synthesis of Carbohydrate-Containing Polyacrylamide Copolymers having the Specificity of 0:3 and 0:4 Factors of Salmonella", Carbohydrate Research, 128:269–282 (1984).
44. Fernandez-Santana, V., et al., "Glycosides of Monoallyl Diethylene Glycol. A New type of Spacer group for Synthetic Oligosaccharides", J. Carbohydrate Chemistry, 8(3), 531–537 (1989).
45. Lee, R. T., et al., "Synthesis of 3-(2-Aminoethylthio) PropylGlycosides", Carbohydrate Research, 37:193–201 (1974).

The disclosure of the above publications, patents and patent applications are herein incorporated by reference in their entirety to the same extent as if the language of each individual publication, patent and patent application were specifically and individually included herein.

BACKGROUND OF THE INVENTION

The anaerobic organism *Clostridium difficile* is the major causative agent of antibiotic-associated bacterial diarrhea and pseudomembranous colitis (PMC) among mainly elderly patients in hospitals and long term care facilities [1,2]. The organism cannot compete successfully with the normal microbial flora in the adult colon, but when the normal intestinal microflora is altered, for example by antibiotic treatment, *C. difficile* is able to colonize the gut in high numbers. Antibiotic therapy accounts for 98% of all cases of *C. difficile* associated diarrhea (CDAD). However, any predisposing condition which alters the normal intestinal flora, including any condition which requires extensive immunosuppressive treatment, can also lead to the development of CDAD. For example, recent evidence suggests that AIDS patients are also high risk candidates for acquiring CDAD [3,4].

*C. difficile* produces two exotoxins, toxin A (an enterotoxin) and toxin B (a cytotoxin) which appear to play important roles in causing CDAD. Toxin A is primarily responsible for the disease. It acts by binding to epithelial cells in the intestine, resulting in the destruction of these cells and causing the secretion of fluid into the intestine. The destruction of these protective epithelial cells by toxin A represents the crucial step leading to the development of diarrhea. Once damage has occurred to the epithelial cells, the potent cytotoxin B can then gain access to underlying sensitive tissues and initiate additional clinical symptoms.

Toxin A has been found to display a lectin-like activity which allows it to bind to an oligosaccharide receptor on epithelial cells. Several oligosaccharide sequences have been identified as potential receptors for toxin A, and include the following structures [5-7]:

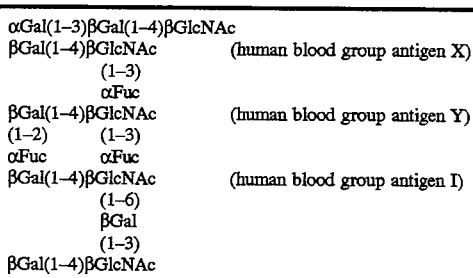

In addition, highly purified toxin A preparations have been obtained using bovine thyroglobulin affinity columns which have terminal αGal(1-3)βGal(1-4)βGlcNAc oligosaccharide sequences [8,9].

The current therapy for patients who suffer from CDAD or PMC is to remove the offending drug and begin oral administration of the antibiotics Metronidazole or Vancomycin along with fluid replacement [3,14]. Vancomycin is only used in certain situations when patients cannot tolerate or are not responsive to Metronidazole treatment. In addition, Vancomycin is not used routinely because of its high cost. This form of therapy is effective in about 80% of the patients who suffer from CDAD or PMC. In about 20% of patients, the diarrhea returns after discontinuing antibiotic treatment [15]. In such individuals, episodes continue to recur until the normal intestinal flora is reestablished and the numbers of *C. difficile* organisms are reduced. This is a slow process, since antibiotics such as Metronidazole, which disturb the balance of the normal intestinal flora, are administered each time the diarrhea occurs.

The only other treatment for CDAD and PMC which removes toxin activity from the intestinal tract involves the use of multigram quantities of anion exchange resins such as cholestyramine and colestipol given orally in combination with antibiotics. This approach has been used to treat mild to moderately ill patients, as well as individuals who suffer from multiple episodes of diarrhea [16,17]. This form of therapy has achieved only moderate success in treatment of the disease [18]. In addition to the lack of efficacy of ion exchange resins, there are several other disadvantages associated with the use of resins. Ion exchange resins do not bind specifically to toxin A. Thus, they may bind to antibiotics themselves, resulting in suboptimal levels of antibiotic within the gut. In addition, if patients are receiving other medications that bind to ion exchange resins, there can be reduced drug levels. A further disadvantage of ion exchange resins is the disagreeable taste and aftertaste which are associated with oral administration of these compounds.

With respect to methods of diagnosis of the presence of toxin A in a sample, one method for detecting *C. difficile* in a sample is to culture the sample. The disadvantages of this method include the length of time required and interference by non-pathogenic, i.e. non-toxin producing, *C. difficile* strains. Other methods involve the use of specific antisera or monoclonal antibodies. U.S. Pat. Nos. 4,863,852 and 5,098,826 describe methods for detecting *C. difficile* toxin A by the use of reagents containing biological receptors for toxin A, including the αGal(1-3)βGal(1-4)βGlcNAc, X and Y antigen oligosaccharide sequences, bound to a support.

In view of the above, there is a need for a compound which would treat antibiotic associated diarrhea. A preferred compound would be administered noninvasively, such as orally.

SUMMARY OF THE INVENTION

The invention provides compositions and methods for the treatment of antibiotic associated diarrhea caused by *Clostridium difficile*.

In one aspect, the invention provides a method to bind and remove toxin A from a sample suspected of containing said toxin A, which method comprises contacting said sample with an oligosaccharide sequence covalently attached to a solid, inert support through a non-peptidyl compatible linker arm, wherein said oligosaccharide sequence binds toxin A, under conditions wherein said toxin A is absorbed to said support; and separating the support containing the absorbed toxin A from the sample.

In another aspect, the invention provides a method to treat diarrhea mediated by toxin A in a subject, which method comprises administering to a subject in need of such treatment an effective amount of a composition comprising an oligosaccharide sequence covalently attached to a pharmaceutically acceptable solid, inert support through a non-peptidyl compatible linker arm, wherein said oligosaccharide sequence binds toxin A, and wherein said composition is capable of being eliminated from the gastrointestinal tract.

In a further aspect, the invention provides a pharmaceutical composition useful in treating CDAD and related conditions initiated by toxin A, which composition comprises an oligosaccharide sequence covalently attached to a pharmaceutically acceptable solid, inert support through a non-peptidyl compatible linker arm, wherein said oligosaccharide sequence binds toxin A; and a pharmaceutically acceptable carrier, wherein said composition is capable of being eliminated from the gastrointestinal tract.

BRIEF DESCRIPTION OF THE DRAWINGS

FIG. 1 demonstrates the neutralization of purified toxin A hemagglutination activity using a panel of SYNSORBs containing various oligosaccharide sequences. Several SYNSORBs were found to effectively neutralize toxin A activity.

DETAILED DESCRIPTION OF THE INVENTION

A. Definitions

Figure 2:
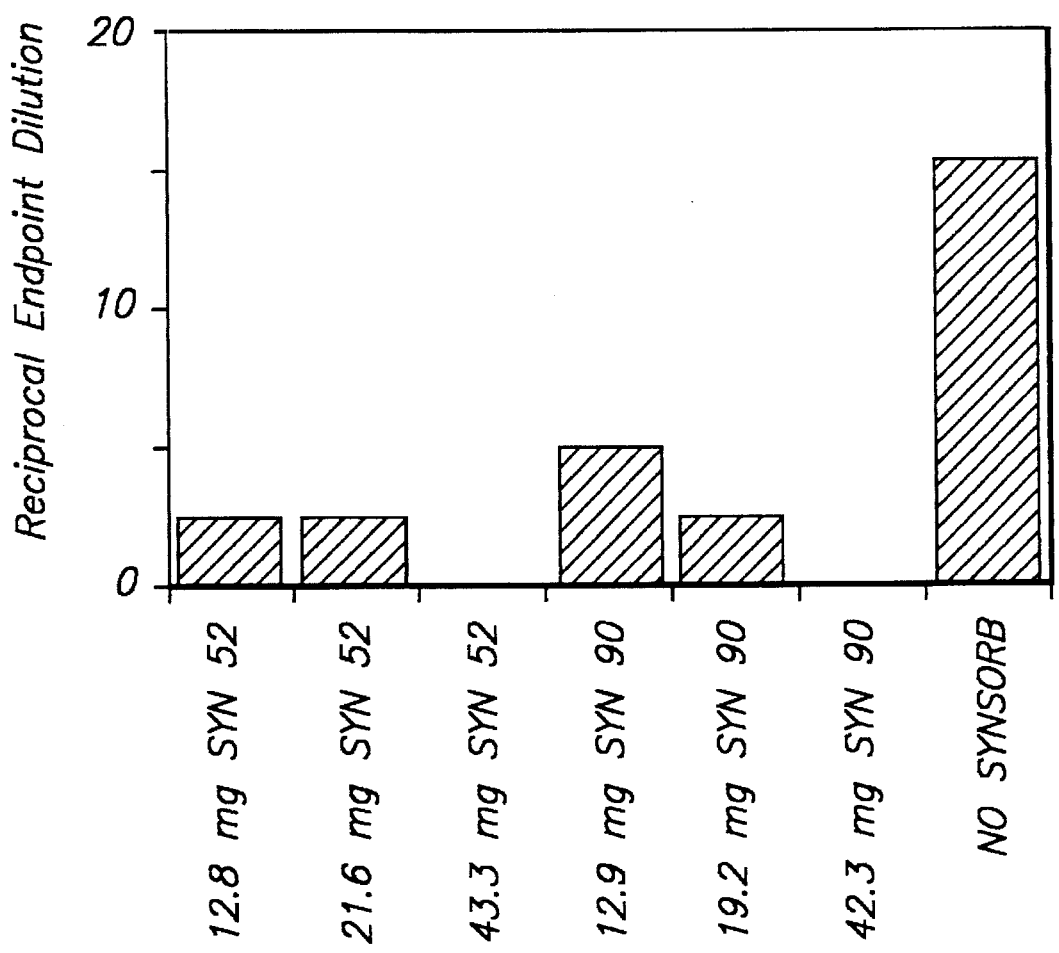
FIG. 2 illustrates the concentration dependent neutralization of toxin A activity using SYNSORB 52 and 90. Both SYNSORBs can effectively neutralize more than about 75% of toxin A activity at a concentration of 20 mg/ml.

As used herein the following terms have the following meanings:

The term "antibiotic-associated bacterial diarrhea" refers to the condition wherein antibiotic therapy disturbs the balance of the microbiol flora of the gut, allowing pathogenic organisms such as *Clostridium difficile* to flourish. These organisms cause diarrhea. Antibiotic-associated bacterial diarrhea includes such conditions as *Clostridium difficile* associated diarrhea (CDAD) and pseudomembranous colitis (PMC).

The term "biocompatible" refers to chemical inertness with respect to human tissues or body fluids.

The term "compatible linker arm" refers to a moiety which serves to space the oligosaccharide structure from the biocompatible solid support and which is biofunctional wherein one functional group is capable of binding to a reciprocal functional group of the support and the other functional group is capable of binding to a reciprocal functional group of the oligosaccharide structure. Compatible linker arms preferred in the present invention are non-peptidyl spacer arms.

The term "pseudomembranous colitis" (PMC), also known as pseudomembranous enterocolitis or enteritis, refers to the inflammation of the mucous membrane of both small and large intestine with the formation and passage of pseudomembranous material (composed of fibrin, mucous, necrotic epithelial cells and leukocytes) in the stools.

The term "solid support" refers to an inert, solid material to which the oligosaccharide sequences may be bound via a compatible linker arm. Where use is in vivo, the solid support will be biocompatible.

The term "SYNSORB" refers to synthetic 8-methoxycarbonyloctyl oligosaccharide structures covalently coupled to Chromosorb P™ (Manville Corp., Denver, Colo.) (12), which is a derivitized silica particle.

The term "toxin A" refers to an enterotoxin of *Clostridium difficile* which initiates CDAD and related conditions. This toxin has a lectin-like activity.

For purpose of this application, all sugars are referenced using conventional three letter nomenclature. All sugars are assumed to be in the D-form unless otherwise noted, except for fucose, which is in the L-form. Further all sugars are in the pyranose form.

B. Synthesis

Chemical methods for the synthesis of oligosaccharide structures can be accomplished by methods known in the art. These materials are generally assembled using suitably protected individual monosaccharides.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the art and can be attached with the proper configuration to the anomeric center of the reducing unit.

Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature [21–37].

The solid supports to which the oligosaccharide structures of the present invention are bound may be in the form of sheets or particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Preferably the solid supports have a particle size of from about 10 to 500 microns for in vivo use. In particular, particle sizes of 100 to 200 microns are preferred.

The oligosaccharide structure(s) is covalently bound or noncovalently (passively) adsorbed onto the solid support. The covalent bonding may be via reaction between functional groups on the support and the compatible linker arm of the oligosaccharide structure. It has unexpectedly been found that attachment of the oligosaccharide structure to the biocompatible solid support through a compatible linking arm provides a product which, notwithstanding the solid support, effectively removes toxin. Linking moieties that are used in indirect bonding are preferably organic biofunctional molecules of appropriate length (at least one carbon atom) which serve simply to distance the oligosaccharide structure from the surface of the solid support.

The compositions of this invention are preferably represented by the formula:

(OLIGOSACCHARIDE-Y-R)$_n$-SOLID SUPPORT where OLIGOSACCHARIDE represents an oligosaccharide group of at least 2 sugar units which group binds to toxin A, Y is oxygen, sulfur or nitrogen, R is an aglycon linking arm of at least 1 carbon atom, SOLID SUPPORT is as defined above, and n is an integer greater than or equal to 1. Oligosaccharide sequences containing about 2 to 10 saccharide units may be used. Sequences with about 3 to 5 saccharide units are preferred.

Numerous aglycon linking arms are known in the art. For example, a linking arm comprising a para-nitrophenyl group (i.e., —OC$_6$H$_4$pNO$_2$) has been disclosed [38]. At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur has been disclosed [39]. Specifically, the linking arm is derived from a 2-bromoethyl group which, in a substitution reaction with thionucleophiles, has been shown to lead to linking arms possessing a variety of terminal functional groups such as —OCH$_2$CH$_2$SCH$_2$CO$_2$CH$_3$ and —OCH$_2$CH$_2$SC$_6$H$_4$— pNH$_2$. These terminal functional groups permit reaction to complementary functional groups on the solid support, thereby forming a covalent linkage to the solid support. Such reactions are well known in the art.

A 6-trifluoroacetamido-hexyl linking arm (—O—(CH$_2$)$_6$—NHCOCF$_3$) has been disclosed [40] in which the trifluoroacetamtdo protecting group can be removed, unmasking the primary amino group used for coupling.

Other exemplifications of known linking arms include the 7-methoxycarbonyl-3,6,dioxaheptyl linking arm [41] (—OCH$_2$—CH$_2$)$_2$OCH$_2$CO$_2$CH$_3$); the 2-(4-methoxycarbonylbutancarboxamido)ethyl [42] (—OCH$_2$CH$_2$NHC(O) (CH$_2$)$_4$CO$_2$CH$_3$); the allyl linking arm [43] (—OCH$_2$CH=CH$_2$) which, by radical co-polymerization with an appropriate monomer, leads to co-polymers; other allyl linking arms [44] are known [—O(CH$_2$CH$_2$O)$_2$CH$_2$CH=CH$_2$]. Additionally, allyl linking arms can be derivatized in the presence of 2-aminoethanethiol [45] to provide for a linking arm —OCH$_2$CH$_2$CH$_2$SCH$_2$CH$_2$NH$_2$. Other suitable linking arms have also been disclosed [21–23, 25, 26].

The particular linking employed to covalently attach the oligosaccharide group to the solid support is not critical.

Preferably, the aglycon linking arm is a hydrophobic group and most preferably, the aglycon linking arm is a hydrophobic group selected from the group consisting of $$-(CH_2)_8C(O)-, \quad -(CH_2)_5OCH_2CH_2CH_2- \text{ and } -(CH_2)_8CH_2O-.$$

We have found that synthetic oligosaccharide sequences covalently attached to a biocompatible solid support, e.g., Chromosorb P™ (SYNSORB) may be used to bind toxin A. These compositions are useful to treat CDAD and PMC. SYNSORB is particularly preferred for these compositions because it is non-toxic and resistant to mechanical and chemical deposition. In studies using rats (a widely accepted model for preclinical studies, since they are predictive of human response), SYNSORBs have been found to pass unaffected through the rat gastrointestinal tract. They were found to be eliminated completely and rapidly (99% eliminated in 72 hours) following oral administration.

Additionally, the high density of oligosaccharide moieties on SYNSORB is particularly useful for binding toxin A, since the toxin is thought to possess multiple oligosaccharide binding sites [11].

Non-peptidyl linking arms are preferred for use as the compatible linking arms of the present invention. The use of glycopeptides is not desirable because glycopeptides contain several, often different, oligosaccharides linked to the same protein. Glycopeptides are also difficult to obtain in large amounts and require expensive and tedious purification. Likewise, the use of BSA or HSA conjugates is not desirable due to questionable stability in the gastrointestinal tract when given orally.

Covalent attachment of an oligosaccharide group containing a toxin A binding unit through a non-peptidyl spacer arm to an inert solid support permits efficient binding and removal of toxin A from a sample to be analyzed for the presence of toxin A or from the intestine of a patient suffering from CDAD. When the oligosaccharide is synthesized with this compatible linker arm attached (in non-derivatized form), highly pure compositions may be achieved which can be coupled to various solid supports.

C. Pharmaceutical Compositions

The methods of this invention are achieved by using pharmaceutical compositions comprising one or more oligosaccharide structures which bind toxin A attached to a solid support.

When used for oral administration, which is preferred, these compositions may be formulated in a variety of ways. It will preferably be in liquid or semisolid form. Compositions including a liquid pharmaceutically inert carrier such as water may be considered for oral administration. Other pharmaceutically compatible liquids or semisolids, may also be used. The use of such liquids and semisolids is well known to those of skill in the art.

Compositions which may be mixed with semisolid foods such as applesauce, ice cream or pudding may also be preferred. Formulations, such as SYNSORBs, which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The SYNSORB itself may also be used without the addition of inert pharmaceutical carriers, particularly for use in capsule form.

Doses are selected to provide neutralization and elimination of the toxin A found in the gut of the effected patient. Useful doses are from about 0.25 to 1.25 micromoles of oligosaccharide/kg body weight/day, preferably about 0.5 to 1.0 micromoles of oligosaccharide/kg body weight/day. Using SYNSORB compositions, this means about 0.5 to 1.0 gram SYNSORB/kg body weight/day, which gives a concentration of SYNSORB in the gut of about 20 mg/ml. Administration is expected to be 3 or 4 times daily, for a period of one week or until clinical symptoms are resolved. The dose level and schedule of administration may vary depending on the particular oligosaccharide structure used and such factors as the age and condition of the subject. Optimal time for complete removal of toxin A activity was found to be about 1 hour at 37° C., using a concentration of SYNSORB of 20 mg in 1 ml sample.

Administration of the oligosaccharide-containing compositions of the present invention during a period of up to seven days will be useful in treating CDAD and PMC.

As discussed previously, oral administration is preferred, but formulations may also be considered for other means of administration such as per rectum. The usefulness of these formulations may depend on the particular composition used and the particular subject receiving the treatment. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid compositions should preferably contain about 1 micromole oligosaccharide/ml.

D. Methodology

We have found that *C. difficile* toxin A may be neutralized by certain oligosaccharide sequences which bind the toxin. In particular, synthetic oligosaccharides covalently attached to solid supports via non-peptidyl compatible linker arms have been found to neutralize toxin A effectively. Examples of such compositions are certain SYNSORBs, which bind and neutralize toxin A activity.

Figure 1:
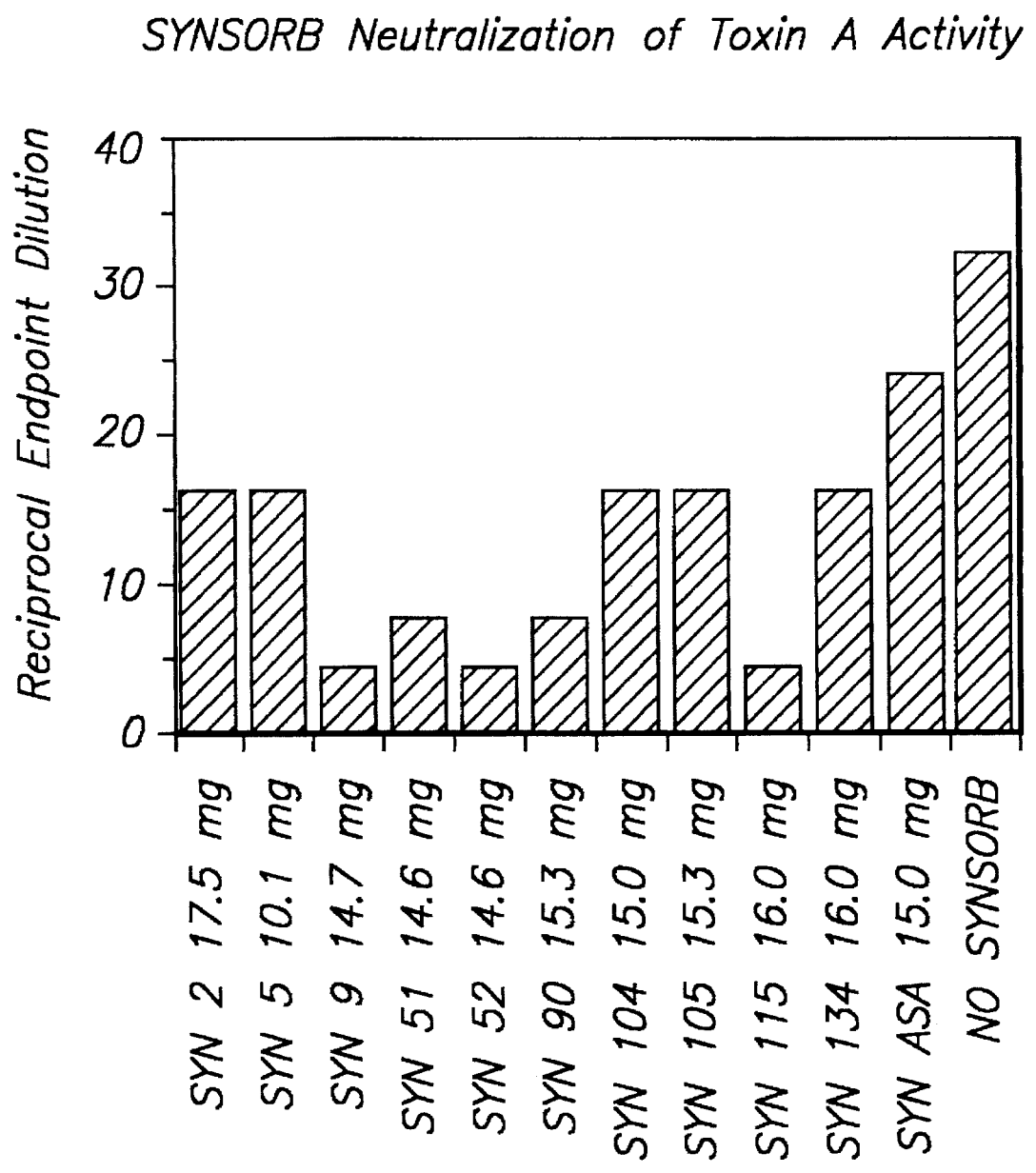
Figure 4:
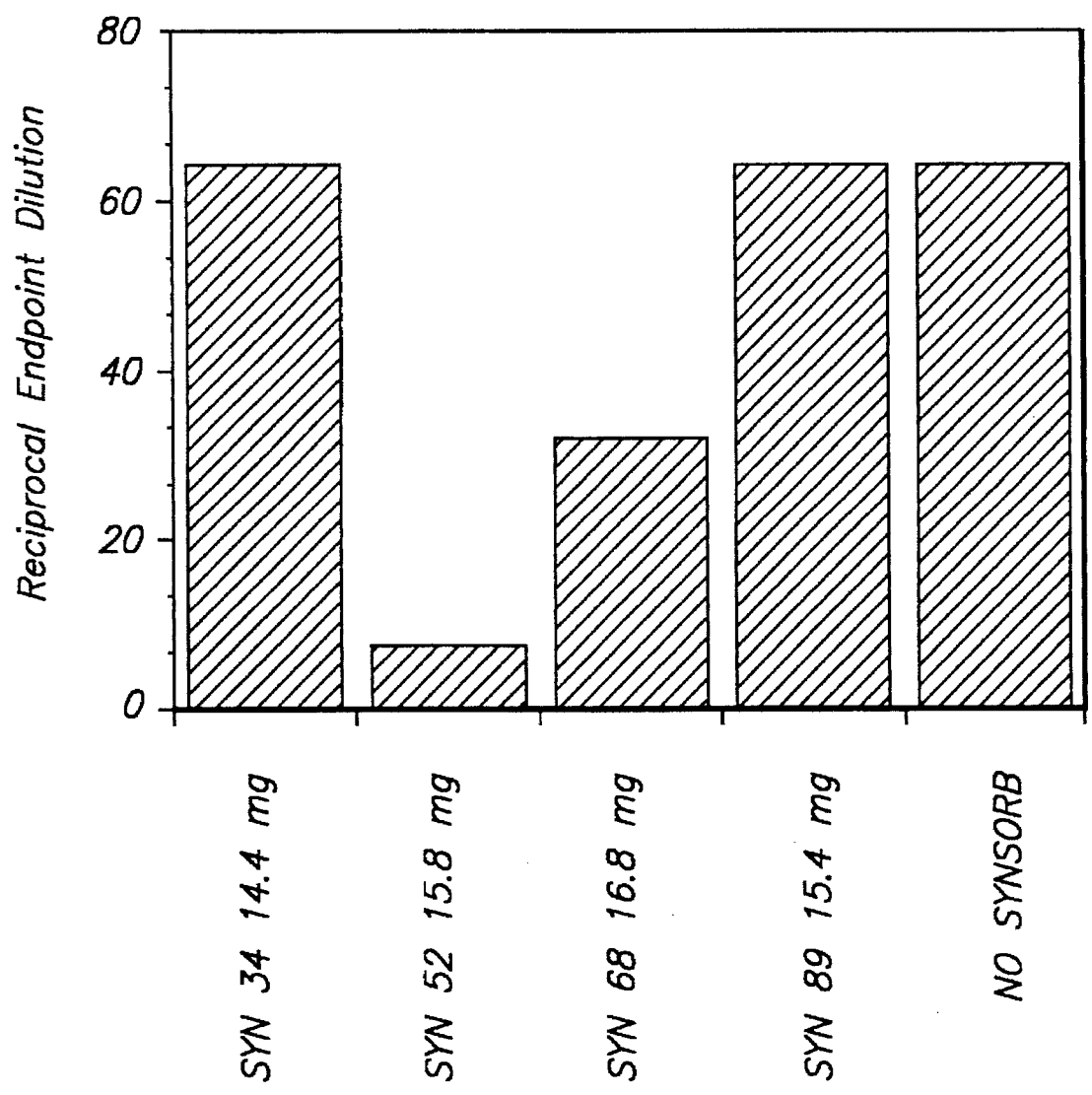
FIG. 4 illustrates the binding affinity of several SYNSORBs for toxin A. Different SYNSORBs were found to have different binding affinities for the toxin.

We have tested the ability of several oligosaccharide sequences attached to Chromosorb P via an 8-methoxylcarbonyloctyl (MCO) spacer arm to neutralize toxin A. The structures tested, also referred to as SYNSORBs, are presented in Table 1. As shown in FIGS. 1 and 4, the SYNSORBs tested varied in their ability to neutralize at least about 50% of the toxin A activity.

The oligosaccharide sequences attached to solid supports useful in the present invention are those which bind toxin A. The binding affinity of an oligosaccharide to toxin A is readily detectable by a simple in vitro test, as for example, set forth in Example 4 below. For the purposes of this invention, oligosaccharide sequences attached to solid supports which bind toxin A means those compositions which reduce endpoint titers from hemagglutination assays by at least 50%.

Certain of the SYNSORBs tested as described above were then used to study the ability of these oligosaccharide compositions to neutralize toxin A in human stool samples.

The binding of shiga-like toxins (SLTs) to chemically synthesized oligosaccharide sequences has been studied [10].

SLTs are a group of cytoxins which are made up of two parts: an A subunit and a B oligomer. The B oligomer is the binding portion of the toxin that allows it to bind to host cell receptors. The SLT toxins bind to glycolipid receptors containing the αGal(1-4)βGal determinant. The A subunit has an enzymatic activity (N-glycosidase) that depurinates 28S ribosomal RNA in mammalian cells. This enzymatic activity abolishes the ability of the toxin-infected cell to perform protein synthesis.

The site for SLT action is endothelial cells found in the kidneys and mesenteric vasculature, and SLTs may cause damage that can result in renal failure and hemoglobin in the urine. SLTs are the causative agent in the hemolytic-uremic syndrome. SLTs may also be partially involved in the pathogenesis of hemorrhagic colitis (bloody diarrhea).

In contrast, toxin A is an enterotoxin that induces fluid secretion, mucosal damage and intestinal inflammation. It serves as a chemoattractant for human neutrophils. Toxin A is a single protein. It cause activation and results in the release of cytokines in monocytes. These inflammatory effects may play an important role in inducing the colonic inflammation seen in pseudomembranous colitis.

Toxin A appears to bind to a glycoprotein receptor, the structure of which has yet to be determined. The mechanism of action is not totally understood, but toxin A is thought to enter cells via receptor-mediated endocytosis and affect the actin cytoskeleton of the cell. The toxin A receptor is thought to be linked to a guanine regulatory protein. Toxin A is the first step in the production of CDAD and PMC.

Previous studies defining the oligosaccharide binding specificity of toxin A have identified several structural requirements for toxin binding [5–7]. Oligosaccharides which terminate in the α-Gal(1-3)βGal sequences attached to the type 2 core (βGal(1-4)βGlCNAc) have been shown to be important for binding. In addition, toxin A also recognizes oligosaccharides with fucose attached to the 2 hydroxyl of galactose or the 3 hydroxyl of N-acetylglucosamine of the type 2 core. The SYNSORBs chosen for toxin neutralization studies include carbohydrates which incorporate these structural features as well as other oligosaccharides which encompass the type 6 (βGal(1-4)βGlc) and type 1(βGal(1-3)βGlcNAc) core structures. Additional SYNSORBs selected for binding studies contain oligosaccharide sequences previously shown to bind to toxin A.

The amount of toxin A adsorption to SYNSORB was determined by assaying supernatants for reduction of endpoint titers in hemagglutination assays relative to controls without any added SYNSORB. Results are shown in FIG. 1. Those SYNSORBs which possessed the X, Y, and αGal(1-3)βGal(1-4)βGlcNAc oligosaccharide sequences (SYNSORBs 51, 52, and 115) were found to effectively remove toxin A activity by 75, 88, and 88%, respectively. In addition, two other SYNSORBs which contained oligosaccharide sequences not previously shown to bind toxin A (SYNSORBs 9 and 90) were as effective at neutralizing toxin A activity. SYNSORBs 2, 5, 104, 105, and 134 neutralized about 50% of toxin A activity. The control SYNSORB (ASA), which contains only the MCO spacer arm only slightly neutralized toxin A activity.

Thus, we have found that the ability to neutralize toxin A is directly related to the oligosaccharide sequences attached to the inert support. The results in FIG. 1 show the importance of the αGal(1-3)βGal linkage for high affinity toxin binding. In addition, we have found that oligosaccharide sequences which possess a β(1-4) linkage between galactose and either N-acetylglucosamine (type 2 core) or glucose (type 6) show high affinity toxin binding. We have further found that toxin A binds oligosaccharide sequences having fucose attached to the 2 hydroxyl of galactose only.

The results presented in FIGS. 1 and 4 show reduction in endpoint titers from hemagglutination assays. Similar results were obtained in tissue culture assays using Chinese Hamster Ovary (CHO) cells. These studies demonstrated that the CHO cells showed a reduction in endpoint dilution relative to controls when SYNSORB was added to purified toxin A preparations.

Several different oligosaccharide sequences attached to solid supports via compatible linker arms have been found to have the ability to neutralize toxin A activity. These sequences, and others that also bind toxin A, may be used to treat CDAD and PMC. Optimal time for complete removal of toxin A activity was found to be about 1 hour at 37° C., using a concentration of SYNSORB of 20 mg in 1 ml sample. Since each gram of SYNSORB contains approximately 0.25 to 1.0 micromoles oligosaccharide, the total amount of oligosaccharide to be given in a daily dose would range from 7.5 to 30 micromoles, using a gut volume of four liters.

The utility of oligosaccharide sequences attached to a solid support via a compatible linker arm to treat CDAD and PMC was also demonstrated by the ability of SYNSORB compositions to neutralize toxin A in human stool samples. These tests on human samples are predictive of in vivo results, since there are essentially no compositional or chemical changes between the in vitro conditions of this assay and in vivo conditions. Further, the assay conditions approximate the actual conditions found in the human intestine. This test has been accepted by those skilled in the art as appropriately correlated with human utility.

The results, shown in Table 2, show that SYNSORB 52 was effective in neutralizing toxin A activity in human stool samples. Generally, greater amounts of toxin in watery stools were more effectively neutralized. The toxin in solid stool samples containing only low levels of toxin was less effectively neutralized.

Treatment of CDAD or PMC may be accomplished by oral administration of compositions containing oligosaccharide sequences covalently bound to a solid support via a compatible linker arm (e.g. SYNSORBs). For example, the SYNSORB has been found to pass through the stomach of rats intact. It then contacts the toxin A in the intestinal tract. Subsequent elimination of the intact SYNSORB with toxin A bound to it results in elimination of toxin A from the patient.

Oligosaccharide sequences covalently attached via compatible linker arms to solid support, e.g. SYNSORBs, are useful to treat individuals who suffer from multiple episodes of diarrhea. Upon initial reoccurrence of diarrhea, patients would be treated with SYNSORB to remove toxin A from the intestine. The removal of toxin A prevents the initial tissue damage to the intestinal lining, which leads to prevention or reduction of diarrhea. No further treatment with antibiotics need be given, allowing the re-establishment of the normal intestinal microflora within the gut. The advantage of such treatment is that it does not affect the recolonization of the intestinal tract by normal microflora. Treatment until discontinuance of diarrhea would allow complete recovery.

In addition to its usefulness in patients suffering from recurring diarrhea, treatment with oligosaccharide sequences covalently attached via compatible linker arms to solid supports, e.g. SYNSORBs, may be used to treat all individuals who suffer from or are prone to develop CDAD or PMC. The use of SYNSORB in combination with antibiotic therapy will be able to reduce the diarrhea more effectively, leading to more rapid recovery.

A major aspect of the invention is the rapid efficient binding of physiological concentration of toxin A present in biological samples, thus permitting assay of the presence and/or quantity of toxin A in these samples. Typically, the biological sample will be a stool sample. The sample may be extracted and prepared using standard extraction techniques. The sample or extract is then contacted with the toxin-binding oligosaccharide sequences covalently bound to solid supports via a compatible linker arm under conditions where any toxin A in the sample is absorbed.

Toxin A may be measured directly on the surface of the oligosaccharide-containing support using any suitable detection system. For example, radioactive, biotinylated or fluorescently labelled monoclonal or polyclonal antibodies specific for toxin A may be used to determine the amount of toxin A bound to the support. A wide variety of protocols for detection of formation of specific binding complexes analogous to standard immunoassay techniques is well known in the art.

Examples

The following methods were used to perform the studies in the Examples that follow.

1. Toxin A purification:

Toxin A was isolated from a toxin producing strain of *C. difficile* (ATCC 43255, VPI strain 10463) using slight modifications of the method of Sullivan et al. [13].

*C. difficile* was grown in 2.3 liter of brain heart infusion broth (BHIB) in anaerobic jars for 72 hours at 37° C. The crude culture was centrifuged at 5,000× g for 20 minutes to sediment the bacteria. The resulting culture supernatant was carefully removed and solid ammonium sulfate (897 g) was added to make 60% saturation. The culture supernatant was stirred at 4° C. overnight and then centrifuged at 10,000× g for 30 minutes. The resulting pellet was dissolved in a minimum amount of buffer A (50 mM sodium phosphate buffer, pH 7.5), dialyzed against 2–4 liter changes of buffer A and concentrated by ultrafiltration using a YM 100 (100, 000 molecular weight cutoff) membrane.

The concentrated toxin-containing solution was loaded onto a DEAE-Sephadex A-25 column (2.5×20 cm) equilibrated with buffer A. After washing the ion exchange resin with buffer A to remove non-adherent protein, the column was developed with a stepwise salt gradient by washing with buffer A containing increasing amounts of NaCl ranging from 0.1 to 0.4M. Toxin A activity was eluted from the column with buffer A containing 0.25M NaCl, while toxin B activity was removed with 0.4M NaCl buffer A.

The overall purity and amount of toxin from each fraction was determined by measuring the protein concentration, as well as using a cytotoxic endpoint using Chinese hamster ovary (CHO) cells. The amount of toxin A activity was also determined by measuring the hemagglutination activity using rabbit erythrocytes. The toxin B fraction was devoid of toxin A activity, as determined by the inability of the toxin B-containing fraction to hemagglutinate rabbit erythrocytes.

2. Hemagglutination Assays Using Rabbit Erythrocytes

Fresh rabbit erythrocytes were washed once in phosphate buffered saline (PBS) and resuspended at a concentration of 4% (v/v) in cold PBS. Serial 2-fold dilutions (50 µl) of toxin A-containing solutions were made in cold PBS in U-shaped microtiter wells. An equal volume (50 µl) of rabbit erythrocytes was then added to each well and the microtiter plate was mixed gently. After incubating the plate for 4 hours at 4° C., the hemagglutination titer was visually assessed.

3. Assay of Toxin Activity Using Chinese Hamster Ovary Cells

The cytotoxic activity of toxin A was measured by the use of Chinese Hamster Ovary (CHO) cells that were maintained in Hams F12 media supplemented with 10% fetal bovine serum in an atmosphere of 5% $CO_2$ at 37° C.

Toxin A samples to be tested were diluted 1:10 in Hams media and filter sterilized through 0.22 micron syringe filters. Samples to be tested were serial 5-fold diluted in media and 100 µl of each dilution was added to wells with confluent monolayers of CHO cells, then incubated for 24 hours at 37° C. in an atmosphere of 5% $CO_2$. Each sample was analyzed in duplicate.

Cytotoxic effects were readily visible after 24 hour incubation by comparing wells with controls that did not contain toxin A. After 24 hours, the cells were fixed with 95% methanol and stained with Giemsa stain. Percent neutralization in the neutralization studies was determined by comparing the endpoint dilutions of samples with and without SYNSORB.

The following examples are offered to illustrate this invention and are not meant to be construed in any way as limiting the scope of this invention.

EXAMPLE 1

Screening of Oligosaccharide-containing Solid Supports for the Ability to Neutralize Toxin A Activity A solution containing purified toxin A prepared as described above (0.5 ml) was added to various SYNSORBs containing different oligosaccharide sequences covalently attached to a solid support via an MCO compatible linker arm. The amount of SYNSORB used ranged from 10.1 to 17.5 mg. The samples were prepared in 1.5 ml microcentrifuge tubes which were incubated at room temperature for 2 hours on an end-over-end rotator.

After incubation, the SYNSORB was allowed to settle to the bottom of the tubes and the supernatants were carefully removed. Serial 2-fold dilutions of the supernatants were prepared and the hemagglutination endpoint determined as described above.

The extent of reduction in the endpoint in the presence of SYNSORB was determined by comparing the endpoint with that of controls in which SYNSORB was not added. An additional control utilized SYNSORB (ASA) that contained only the MCO (hydrophobic 8 carbon) spacer arm.

Results are shown in FIG. 1, and demonstrate that several oligosaccharide structures were found to effectively neutralize toxin A activity.

EXAMPLE 2

Determination of Optimal Binding Conditions Using SYNSORBs 52 and 90

The amount of SYNSORBS 52 and 90 required for maximal toxin A neutralization was determined by adding 1 ml of a purified toxin A solution to pre-weighed amounts of each SYNSORB in 1.5 ml microcentrifuge tubes. SYNSORB 52 samples were tested using 12.8, 21.6 and 43.3 mg amounts of SYNSORB 52; SYNSORB 90 samples were tested using 12.9, 19.2 and 42.3 mg amounts of SYNSORB 90. Samples were incubated for 2 hours at 37° C. on an end-over-end rotator. Control samples containing only toxin A solution were also tested.

The amount of neutralization in each sample was determined by comparing the endpoint titers of hemagglutination assays from samples with and without SYNSORB. The results, shown in FIG. 2, demonstrate that about 20 mg of each SYNSORB tested was able to neutralize at least 75% of the toxin A in 1 ml of toxin A solution.

The length of incubation time required for optimal neutralization was determined by incubating microcentrifuge tubes containing 1 ml of purified toxin A solution and 20 mg of either SYNSORB 52 or SYNSORB 90. Samples were incubated at 37° C. on an end-over-end rotator for 10, 20, 40, 80 or 160 minutes.

Figure 3:
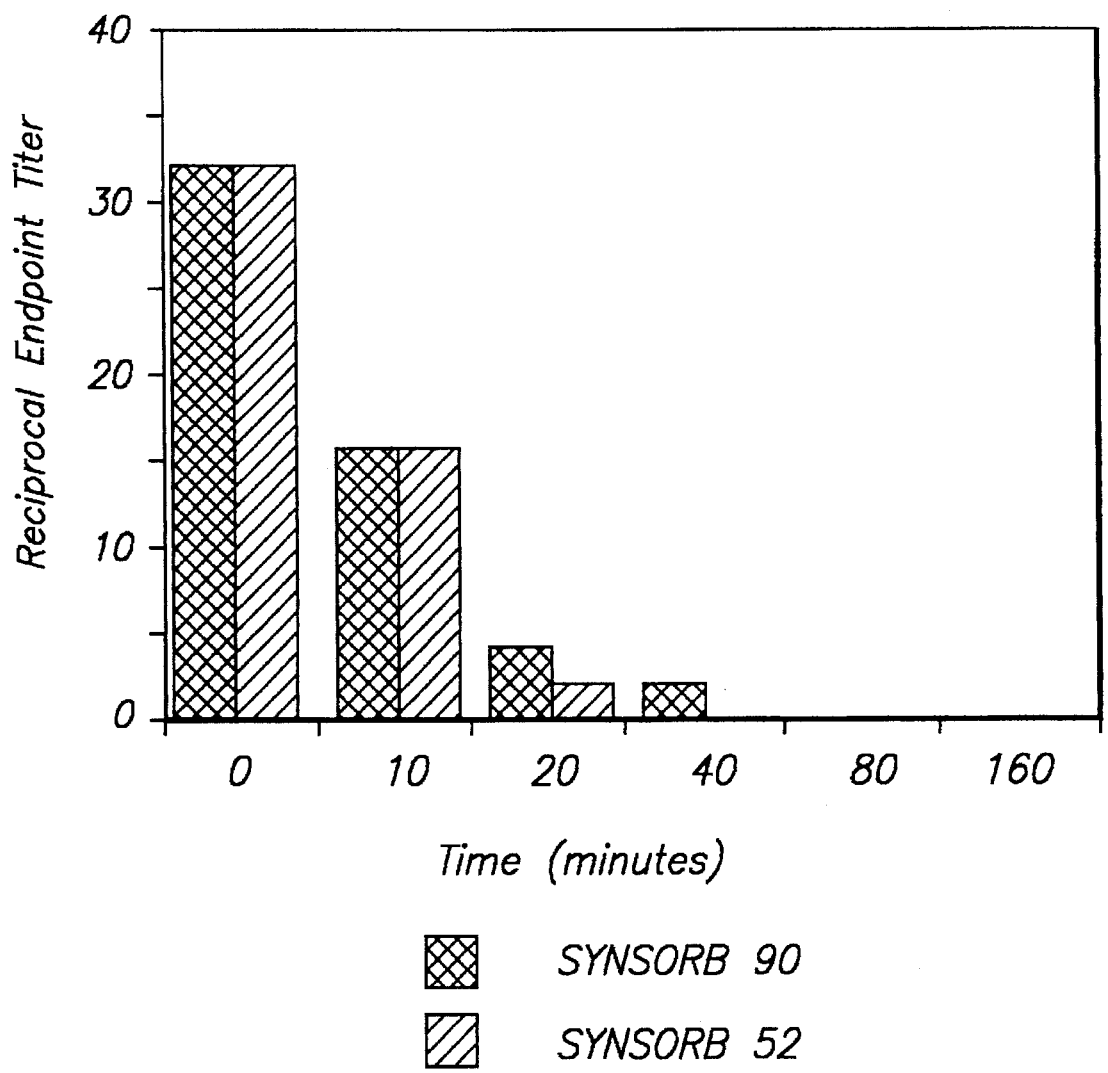
FIG. 3 demonstrates the time dependency of neutralization of toxin A activity using SYNSORB 52 and 90 at a concentration of 20 mg/ml.

The degree of neutralization at each incubation period was determined as described above. The results, shown in FIG. 3, demonstrate that about 1 hour incubation (between 40 and 80 minutes) resulted in effective neutralization of toxin A.

EXAMPLE 3

Neutralization of Toxin A Activity in Toxin-Positive Human Stool Samples

Toxin A positive human stool samples were obtained from University of Alberta Hospital's Microbiology Laboratory. One ml of each stool sample was placed in a 1.5 ml microcentrifuge tube, 20 mg SYNSORB 52 (pre-wetted with 50 µl PBS) was added, and the tubes were incubated on an end-over-end rotator for 4 hours at 37° C. Control stool samples without SYNSORB were also tested simultaneously. After incubation the stool samples were centrifuged at 14,000 rpm in an Eppendorf Microcentrifuge for 10 minutes. The resulting supernatants were carefully removed and placed into clean microcentrifuge tubes.

The amount of toxin A in each sample was determined by using the PREMIER™ *C. difficile* Toxin A detection kit (Meridian Diagnostics, Cincinnati, Ohio). The percent neutralization was assessed by measuring the reduction in the absorbance at 450 nm relative to individual control samples without added SYNSORB.

Results, shown in Table 2, demonstrate that SYNSORB 52 was able to neutralize toxin A activity in human biological samples.

EXAMPLE 4

Determination of Binding Affinity

To assess the binding affinity of various SYNSORBs to toxin A, each SYNSORB was combined with toxin A as described in Example 1. Endpoint titers from hemagglutination assays using rabbit erythocytes were determined as described previously. SYNSORBs that were more effective at neutralizing toxin A activity possessed oligosaccharide structures that bound to toxin A with higher affinities. Those SYNSORBs which reduced titers by greater than 50% were deemed to bind toxin A.

Results are shown in FIG. 4, and demonstrated that some SYNSORBs (SYNSORBs 52 and 68) bind toxin A by this criteria, while others (SYNSORBs 34 and 89) appear not to bind toxin A.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

TABLE 1

SYNSORBs utilized in toxin A neutralization studies

| SYN-SORB Number | Structure Number | Common Name | Oligosaccharide Structure* |
|---|---|---|---|
| 2 | 1 | B | αGal(1–3)βGal (1–2) αFuc |
| 5 | 2 | H Type 2 | βGal(1–4)βGlcNAc (1–2) αFuc |
| 9 | 3 | B Type 2 | αGal(1–3)βGal(1–4)βGlcNAc (1–2) αFuc |
| 34 | 4 | N-Acetyllactosamine | βGal(1–4)βGlcNAc |
| 51 | 5 | X | βGal(1–4)βGlcNAc (1–3) αFuc |
| 52 | 6 | Y | βGal(1–4)βGlcNAc (1–2) (1–3) αFuc αFuc |
| 68 | 7 | Pk | αGal(1–4)βGal(1–4)βGlc |
| 89 | 8 | sialyllactose | αNeuAc(2–6)βGal(1–4)βGlc |
| 90 | 9 | — | αGal(1–3)βGal(1–4)βGlc |
| 104 | 10 | H Type 6 | βGal(1–4)βGlc (1–2) αFuc |
| 105 | 11 | B Type 6 | αGal(1–3)βGal(1–4)βGlc (1–2) αFuc |
| 115 | 12 | — | αGal(1–3)βGal(1–4)βGlcNAc |
| 134 | 13 | — | αGal(1–3)βGal(1–3)βGlcNAc |

*All oligosaccharides are linked to Chromosorb P through the standard hydrophobic 8 carbon spacer arm.

TABLE 2

Neutralization of toxin A activity in stool samples with SYNSORB 52

| Toxin A Levels in Stool Samples$^a$ | Type of Stool$^b$ | Percent Neutralization |
|---|---|---|
| ++++ | SS | 96 |
| ++++ | SW | 80 |
| ++++ | SW | 77 |
| ++++ | W | 70 |
| ++++ | SS | 64 |
| +++ | SW | 63 |
| ++ | W | 80 |
| ++ | W | 72 |
| ++ | SW | 46 |
| + | S | 50 |
| + | S | 42 |
| + | W | 35 |
| + | W | 0 |

$^a$Toxin A levels in stool samples were determined by the

TABLE 2-continued use of PREMIER™ *C. difficile* Toxin A detection kit. The positive signs in Table 2 represent the relative amount of toxin A in each sample as determined by the absorbance at 450 nm as shown below. The mean percent neutralization using SYNSORB 52 with respect to toxin A levels in stool samples are also shown.

| | $A_{450}$ | Mean Percent Neutralization |
|---|---|---|
| ++++ | >1.5 | 77 ± 12% (n = 5) |
| +++ | 1.1–1.4 | 63% (n = 1) |
| ++ | 0.6–1.0 | 66 ± 18% (n = 3) |
| + | 0.1–0.4 | 32 ± 22% (n = 3) |

$^b$The overall consistency of the stool samples examined. The abbreviations S, SS, SW and W refer to solid, semi-solid, semi-watery and watery respectively. The mean percent neutralization of toxin A activity using SYNSORB 52 with respect to stool consistency are as follows: S(31 ± 27%, n = 3), SS (80 ± 23%, n = 2), SW (67 ± 16%, n = 4) and W (62 ± 19%, n = 4).

What is claimed is:

1. A method to bind and remove toxin A from a sample suspected of containing said toxin A, which method comprises:

a) contacting said sample with an oligosaccharide sequence selected from the group consisting of αGal(1-3)βGal
(1-2)
αFuc;

βGal(1-4)βGlcNAc
(1-2)
αFuc;

αGal(1-3)βGal(1-4)βGlCNAc
(1-2)
αFuc;

βGal(1-4)βGlcNAc;
αGal(1-4)βGal(1-4)βGlc;
αNeuAc(2-6)βGal(1-4)βGlc;
αGal(1-3)βGal(1-4)βGlc;
βGal(1-4)βGlc;
(1-2)
αFuc;
αGal(1-3)βGal(1-4)βGlc;
(1-2)
αFuc; and
αGal(1-3)βGal(1-3)βGlcNAc covalently attached to a solid, inert support through a non-peptidyl compatible linker arm, wherein said oligosaccharide sequence binds toxin A, under conditions wherein said toxin A is absorbed to said support; and b) separating the support containing the absorbed toxin A from the sample.

2. The method of claim 1 wherein said solid, inert support is a biogenic silicate and said non-peptidyl compatible linker arm is —(CH$_2$)$_8$C(O)—.

3. The method of claim 1 wherein said linker arm is —(CH$_2$)$_8$C(O)—.

* * * * *

UNITED STATES PATENT AND TRADEMARK OFFICE

CERTIFICATE OF CORRECTION

PATENT NO. : 5,635,606
DATED : June 3, 1997
INVENTOR(S) : Louis D. Heerze and Glen D. Armstrong It is certified that an error appears in the above-identified patent and that said Letters Patent is hereby corrected as shown below:

In Claim 1, line 12, replace "αGal(1-3)βGal(1-4)βGlCNAc" with -- αGal(1-3)βGal(1-4)βGlcNAc--.

Signed and Sealed this

Twenty-first Day of November, 2000

Attest:

Q. TODD DICKINSON

*Attesting Officer*    *Director of Patents and Trademarks*